United States Patent
Stevens et al.

(10) Patent No.: US 9,737,870 B2
(45) Date of Patent: Aug. 22, 2017

(54) PYROLYTIC REACTOR

(71) Applicant: UOP LLC, Des Plaines, IL (US)

(72) Inventors: Carl J. Stevens, Lake Forest, IL (US); Antoine Negiz, Wilmette, IL (US); Vinayender Kuchana, Hyderabad (IN)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/131,316

(22) Filed: Apr. 18, 2016

(65) Prior Publication Data

US 2016/0228847 A1 Aug. 11, 2016

Related U.S. Application Data

(62) Division of application No. 13/947,404, filed on Jul. 22, 2013, now Pat. No. 9,370,757.

(60) Provisional application No. 61/691,376, filed on Aug. 21, 2012.

(51) Int. Cl.
| | |
|---|---|
| *B01J 19/26* | (2006.01) |
| *B01J 19/02* | (2006.01) |
| *C07C 2/78* | (2006.01) |
| *B01J 3/00* | (2006.01) |
| *B01J 19/24* | (2006.01) |
| *B01J 4/00* | (2006.01) |
| *B01J 6/00* | (2006.01) |

(52) U.S. Cl.
CPC .............. *B01J 19/26* (2013.01); *B01J 3/008* (2013.01); *B01J 4/002* (2013.01); *B01J 6/008* (2013.01); *B01J 19/02* (2013.01); *B01J 19/2415* (2013.01); *C07C 2/78* (2013.01); *B01J 2219/0004* (2013.01); *B01J 2219/00051* (2013.01); *B01J 2219/00094* (2013.01); *B01J 2219/00123* (2013.01); *B01J 2219/00157* (2013.01); *B01J 2219/0204* (2013.01); *B01J 2219/029* (2013.01); *B01J 2219/0263* (2013.01); *B01J 2219/0281* (2013.01); *B01J 2219/0286* (2013.01)

(58) Field of Classification Search
CPC ........ B01J 3/008; B01J 19/2415; B01J 19/26; B01J 4/002; B01J 6/008
See application file for complete search history.

(56) References Cited

U.S. PATENT DOCUMENTS

| | | |
|---|---|---|
| 3,515,519 A | 6/1970 | Sennewald et al. |
| 4,106,912 A | 8/1978 | Dollinger et al. |
| 4,267,160 A | 5/1981 | Kraus et al. |
| 4,724,272 A | 2/1988 | Raniere et al. |
| 4,822,588 A | 4/1989 | Gravley et al. |

OTHER PUBLICATIONS

Extended European Search Report mailed May 20, 2016 in European Application No. 13830926.5.

*Primary Examiner* — Matthew Merkling

(57) ABSTRACT

A pyrolytic reactor comprising a fuel injection zone, a combustion zone adjacent to the fuel injections zone, an expansion zone adjacent to the combustion zone, a feedstock injection zone comprising a plurality of injection nozzles and disposed adjacent to the expansion zone, a mixing zone configured to mix a carrier stream and feed material and disposed adjacent to the feedstock injection zone, and a reaction zone adjacent to the mixing zone. The plurality of injection nozzles are radially distributed in a first assembly defining a first plane transverse to the feedstock injection zone and in a second assembly transverse to the feedstock injection zone.

16 Claims, 3 Drawing Sheets

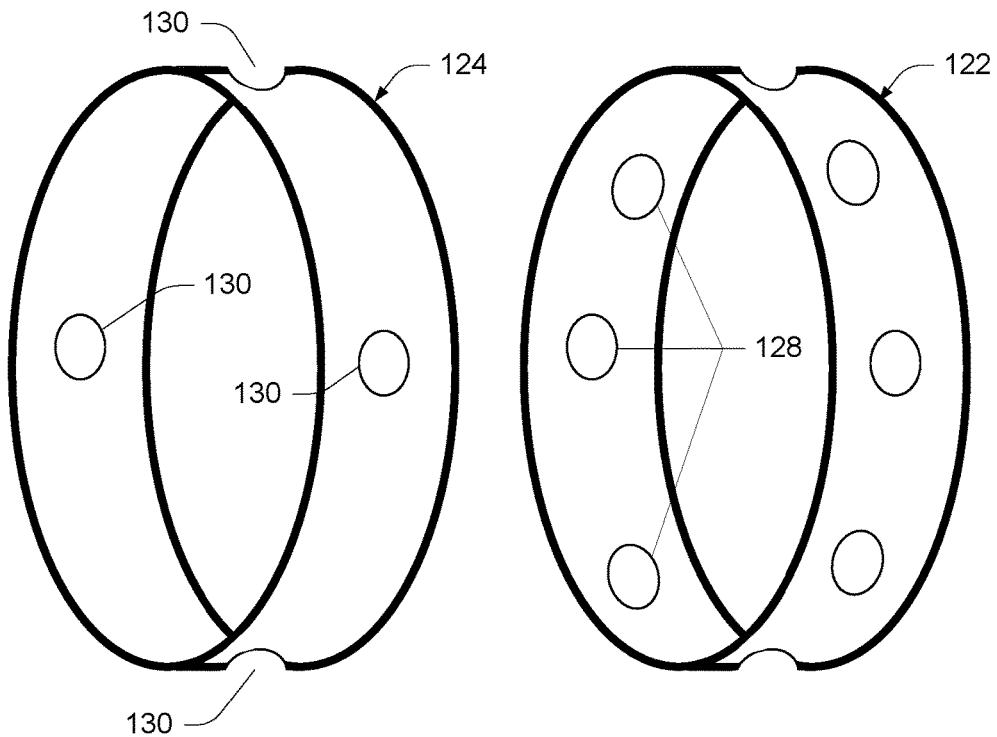
*Fig. 2(a)* *Fig. 2(b)*
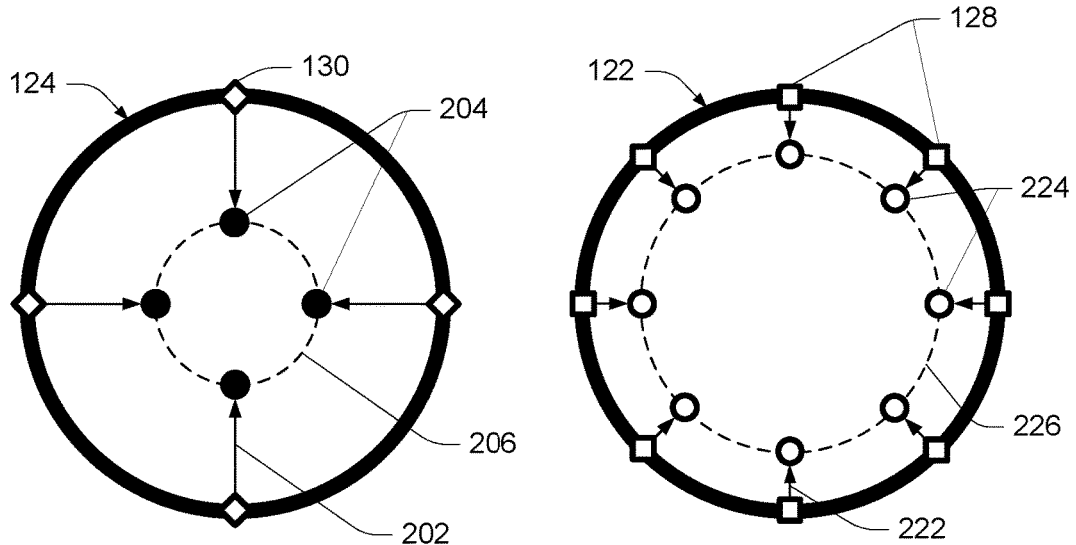
*Fig. 2(c)* *Fig. 2(d)*

PYROLYTIC REACTOR

CROSS-REFERENCE TO RELATED APPLICATIONS

This application is a Division of application Ser. No. 13/947,404 filed on Jul. 22, 2013, and claims priority from Provisional Application No. 61/691,376 filed Aug. 21, 2012, the contents of which are hereby incorporated by reference in its entirety.

FIELD OF THE INVENTION

The disclosure relates in general to a reactor for the pyrolytic processing of hydrocarbons. In certain embodiments, the disclosure relates to injectors to introduce feed material into the reactor. In certain embodiments, the disclosure relates to multiple assemblies of injectors configured to introduce feed material into different portions of the carrier stream within the reactor.

BACKGROUND OF THE INVENTION

Thermal processing techniques are commonly used to convert feedstock hydrocarbon material to more valuable products. For example, various thermal processing techniques are used to convert methane directly to $C_2$ hydrocarbons, such as acetylene via reaction (1), ethylene via reaction (2), and ethane via reaction (3).

$$2CH_4 \rightarrow C_2H_2 + 3H_2 \quad (1)$$

$$2CH_4 \rightarrow C_2H_4 + 2H_2 \quad (2)$$

$$2CH_4 \rightarrow C_2H_6 + H_2 \quad (3)$$

These reactions are highly endothermic, requiring approximately 377 kJ/mol, 202 kJ/mol, and 65 kJ/mol, respectively. In addition, higher temperatures are generally required to achieve high conversion of the feedstock and high selectivity to the desired product.

One type of thermal processing used in the prior art involves exposing the feedstock to high temperature combustion gases causing the feedstock to pyrolyze into the desired unsaturated product. Many traditional processes involve steam cracking. Whereas other processes involve combustion to generate the necessary temperatures.

The formation of acetylene from methane by thermal processing is difficult because of the relative free energies of formation of methane and acetylene. Acetylene and ethylene can continue reacting to form higher dienes and alkynes such as monovinylacetylene, aromatic and polyaromatic compounds which can form undesirable tar and soot. Above 800 K, $C_xH_y$ compounds may undergo decomposition into carbon and hydrogen. Below 1500 K, the free energy of formation of methane is above that of acetylene. As such, the formation of methane, the final product of thermodynamic equilibrium, is favored over acetylene between the temperatures of 800 K and 1500 K. Above 1500 K, however, the free energy of formation of acetylene is lower than that of methane. As a result, the formation of acetylene is favored over that of methane. But, as the reactants are cooled below 1500 K, the thermodynamic equilibrium shifts back to methane and the acetylene produced at the higher temperature will decompose and reform as methane. Acetylene and the other hydrocarbons can continue to react to form aromatic and polyaromatic species. When water and carbon dioxide are present acetylene can react to form carbon monoxide which is a less valuable product than acetylene. Methane is a very refractory material and as such the pyrolitic reaction of methane to form acetylene and other desired hydrocarbons has a high activation energy. The decomposition reactions of acetylene have lower activation energy and thus the formation of acetylene is favored by reacting at high temperatures but with short controlled residence times that minimize consecutive reactions of acetylene with additional acetylene, hydrocarbons and oxygen containing species such as $H_2O$, $CO_2$ and $O_2$.

Certain prior art processes involve combusting a fuel mixture to create a high temperature supersonic carrier stream. A fuel and oxidizer are combusted to produce a hot gas stream at a super-atmospheric pressure and supersonic velocity. Feedstock is injected into the supersonic hot gas stream to initiate the endothermic pyrolysis reactions.

These prior art processes, however, rely on the turbulence of the stream to mix the feedstock within the carrier stream. Increased uniformity of composition and increased uniformity of temperature within the stream during acetylene formation will result in increased conversion and selectivity for the desired product. In prior art processes, feedstock is injected uniformly via a single row of uniform injectors along the wall of the reactor and at a different temperature than the carrier stream. This creates anon-uniform distribution with a stream of highly concentrated, low temperature feedstock alongside the high temperature carrier stream. Prior art reactors therefore included a mixing zone of sufficient length to allow the turbulent flow to mix the feedstock with the carrier stream. Applicants' have determined that improvements in the manner of mixing and/or injecting the feedstock would result in improved methane conversion and acetylene selectivity and/or a reduction in reactor length.

Accordingly, it would be an advance in the state of the art to provide a pyrolytic reactor capable of injecting feedstock into the carrier stream in a manner that (i) minimizes the time required to achieve uniform composition and/or temperature and/or (ii) minimizes the mixing length within the reactor for a given stream velocity, resulting in higher conversion and selectivity for the desired product.

SUMMARY OF THE INVENTION

A pyrolytic reactor is disclosed, wherein the pyrolytic reactor comprises a fuel injection zone, a combustion zone adjacent to the fuel injection zone, an expansion zone adjacent to the combustion zone, a feedstock injection zone comprising a plurality of injection nozzles and disposed adjacent to the expansion zone, a mixing zone configured to mix a carrier stream and feed material and disposed adjacent to the feedstock injection zone, and a reaction zone adjacent to the mixing zone. The plurality of injection nozzles are radially distributed in a first assembly defining a first plane and in a second assembly defining a second plane.

The first plane is transverse to the injection zone. The second plane is transverse to the injection zone. The plurality of injection nozzles in the first assembly are configured to inject feed material into the carrier stream at a first radial penetration depth. the plurality of injection nozzles in the second assembly are configured to inject feed material into the carrier stream at a second radial penetration depth.

BRIEF DESCRIPTION OF THE DRAWINGS

FIGS. 2(a) and 2(b) are perspective views of the injection assemblies of FIG. 1;

FIGS. 2(c) and 2(d) show the radial penetration of feedstock into the reactor body for the injection assemblies of FIG. 1.

DETAILED DESCRIPTION OF THE PREFERRED EMBODIMENTS

Figure 1:
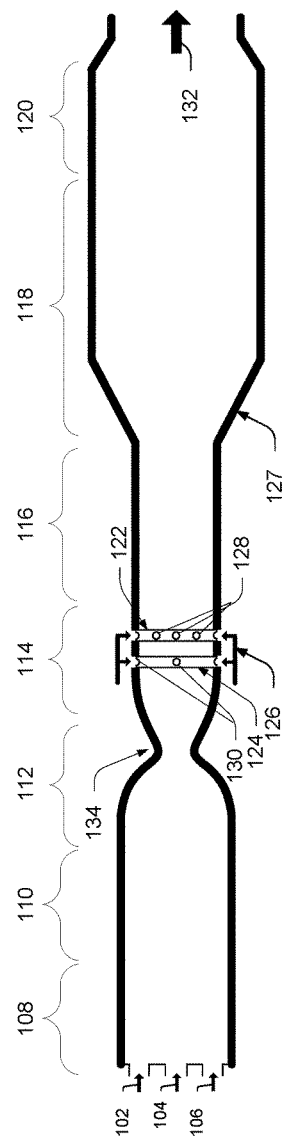
FIG. 1 is longitudinal cross section of a pyrolytic reactor having multiple feedstock injection points arranged in two assemblies.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Applicants' apparatus and method provide a pyrolytic reactor capable of injecting feedstock into a carrier stream in a manner that (i) minimizes the time required to achieve uniform composition and/or temperature and/or (ii) minimizes the mixing length within the reactor for a given stream velocity, resulting in higher conversion and selectivity for the desired product.

In order to achieve reasonable production to acetylene by thermal processing, the reaction mixture is first heated to a temperature exceeding 1500 K to favor the formation of acetylene. Next, a sufficient amount of reaction enthalpy is provided to satisfy the 377 kJ/mol required for the formation of acetylene. If additional energy is not provided, the endothermic nature of the acetylene formation may drive the temperature below 1500 K. Finally, the reaction mixture is quickly cooled at a rate faster than the rate at which the acetylene can decompose into heavier hydrocarbons such as monovinylacetylene, aromatic and polyaromatic species, tar and soot. This quick cooling process is sometimes referred to as "freezing" the reaction when the amount of acetylene is high. It is desirable to initiate the freezing step at conditions near the maximum acetylene formation (i.e., the point where the rate of formation of acetylene from methane balances the decomposition of acetylene to CO, and heavier hydrocarbons) and to complete the freezing step as quickly as possible to prevent the decomposition of any acetylene.

While the present disclosure relates to the pyrolytic conversion of a methane feedstock to acetylene, those skilled in the art will appreciate that the apparatus and methods disclosed herein can be used with other feedstock material to create other products. For example, in one embodiment, Applicants' reactor design and method using same may be used to convert methane to other higher molecular weight hydrocarbons (other than acetylene), such as ethane, ethylene, or higher molecular weight hydrocarbons (i.e., $C_{2+x}H_y$). In general, Applicants' reactor design and method using same may be used to facilitate any endothermic reaction that also requires a high temperature for the reaction to occur, such as, without limitation, steam reforming of hydrocarbons, catalytic naphtha cracking, and dehydrogenation to light olefins, such as propylene and ethylene.

Referring to FIG. 1, a longitudinal cross section of a pyrolytic reactor 100 is depicted. In one embodiment, the reactor 100 is tubular (i.e., the transverse cross section is circular). The high temperatures necessary for the formation of acetylene as well as controlled residence time and rapid quenching can be achieved in the pyrolytic reactor 100. Fuel 102 and an oxidizer 106 are injected in the fuel injection zone 108 at the proximal end of reactor 100. In one embodiment, the fuel comprises hydrogen ($H_2$), the oxidizer comprises oxygen, and the ratio of hydrogen to oxygen is about a 3/1 molar ratio.

In some embodiments, the fuel 102 and oxidizer 106 are mixed prior to injection into the fuel injection zone 108. In some embodiments, the fuel 102 and oxidizer 106 are injected into the fuel injection zone 108 and mixed by turbulance within the fuel injection zone 108. In some embodiments, steam and/or inert gas 104 is also injected into the fuel injection zone. In certain embodiments, the steam and/or inert gas is added in an amount less than about fifty weight percent (50 wt. %). In certain embodiments, the fuel injection zone is further configured with an additional injector to introduce steam into the fuel injection zone.

The fuel and oxidizer are combusted in the combustion zone 110. The combustion heats the carrier gas to a high temperature. In some embodiments, the temperature of the carrier gas reaches up to about 2500 K in the combustion zone 110. In other embodiments, the temperature of the carrier gas reaches up to about 3000 K in the combustion zone 110. In yet other embodiments, the temperature of the carrier gas reaches up to about 3600 K in the combustion zone 110.

The combustion zone 110 is operated at a pressure that is higher than the reactor, which propels the carrier gas toward the distal end of the reactor 100 at high velocity. In some embodiments, the velocity of the carrier gas at the distal end of the combustion zone 110 is below supersonic speed (i.e., less than Mach 1).

In an alternative embodiment the feedstock injection zone can be of an annular cross section. The fuel injection zone, combustion zone, expansion zone, mixing zone and reaction zone may alternatively be either annular or circular. The use of an annular feedstock injection zone reduces the crossflow distance that feed must be injected into the carrier stream. The inner annulus may also be equipped with similar feedstock injection nozzles and can be held in place with struts or secured at the inlet or outlet of the reactor. Struts can have internal channels to allow the flow of feed or coolant. In some embodiments the feedstock injection zone can have other non-circular cross sections that reduce the crossflow distance that feedstock must penetrate into the carrier stream, for example rectangular or elliptical. For the case of a feedstock injection zone with a non-circular cross section the pipe diameter will be understood to mean the hydraulic diameter of the feedstock injection zone.

The subsonic carrier gas enters the expansion zone 112 and flows through a convergent-divergent nozzle 134. The convergent-divergent nozzle 134 transforms a portion of the thermal energy in the carrier stream into kinetic energy, resulting in a sharp increase in velocity of the carrier stream.

The velocity of the carrier gas transitions from subsonic (i.e., less than Mach 1) to supersonic (i.e., greater than Mach 1) within the expansion zone 112. In one embodiment, at the distal end of the expansion zone 112, the temperature of the carrier gas is 1500 K to 2500 K and in another embodiment the temperature of the carrier gas is less than 3000 K. In one embodiment, the average velocity of the carrier gas (across a transverse cross section) is greater than Mach 1. In one embodiment, the average velocity of the carrier gas is about Mach 2 or above.

The methane feedstock is injected into the supersonic carrier gas in the feedstock injection zone 114. In one embodiment, the feedstock is injected at a temperature of 700 K to 1200 K. In one embodiment the feedstock is injected at a temperature of 300 K to 2000 K.

The feedstock is supplied by feed lines 126 and injected via a plurality of injection nozzles 128 and 130, which are arranged in the wall of the feedstock injection zone 114 along two regions (i.e., assemblies) 122 and 124, wherein assembly 122 defines a first traverse plane through reactor 100 and assembly 124 defines a second transverse plane through reactor 100. In one embodiment, the nozzles 128 and 130 are disposed directly in the wall of the feedstock injection zone 114. In one embodiment, the nozzles 128 and 130 are mounted in a circular structure that is inline with the wall of the reactor 100 to form the feedstock injection zone 114. In one embodiment, the nozzles 128 and 130 are mounted in elliptical or other structure that is inline with the wall of the reactor 100 to form the feedstock injection zone 114.

In one embodiment, assembly 122 comprises eight (8) nozzles. In certain embodiments, assembly 122 comprises more than eight nozzles. In certain embodiments, assembly 122 comprises fewer than eight nozzles. In certain embodiments the nozzles of assembly 124 are equally spaced around the perimeter of the feedstock injection zone 114.

In certain embodiments, assembly 124 comprises four (4) nozzles. In certain embodiments, assembly 124 comprises more than four nozzles. In certain embodiments, assembly 124 comprises between about 2 to about 4 injection nozzles. In certain embodiments, the nozzles of assembly 124 are equally spaced around the perimeter of the feedstock injection zone 114. In certain embodiments, assembly 124 comprises fewer nozzles than does assembly 122.

In one embodiment, each of the 8 nozzles in assembly 122 is configured to inject the feedstock into the carrier stream to a depth of about ⅓ the distance to the centerline of the feedstock injection zone 114 (i.e., a radial depth of about ⅓ the distance to the radial midpoint of the feedstock injection zone) and each of the 4 nozzles in assembly 124 are configured to inject the feedstock into the carrier stream to a radial depth of about ⅔. The radial depth of penetration into the carrier stream is a function of the angle at which the feedstock is injected into the carrier stream, the flow rate at each nozzle, the diameter of the nozzle and the velocity of the carrier stream through the feedstock injection zone 114.

The radial depth of penetration of the jet into the carrier stream can be determined by a number of means known to those skilled in the art, such as mathematical correlations, computational fluid dynamic modeling, experimental measurement of concentration, temperature, density. Equation 1 is an example of a mathematical correlation in which a, b, c and d are positive constants, $M_j$ is the Mach number of the jet, $d_j$ is the throat diameter of the injector, $(\rho v^2)_j$ is the momentum of the jet at the throat of the nozzle, $(\rho v^2)_c$ is the momentum of the carrier stream and $\theta$ is the angle of the jet from the downstream wall. The throat of the nozzle is defined as the portion of the nozzle that has the minimum cross sectional area. The radial depth of penetration of the jet into the carrier stream is also impacted by the type of injector. For example an aeroramp injector (examples of which are described in, JOURNAL OF PROPULSION AND POWER Vol. 22, No. 5, September-October 2006, pg 1027 to 1038 and paper AIAA 2005-301 from the American Institute of Aeronautics and Astronautics) can be used to provide deeper penetration of the jet with less pressure loss. For an injector that is not a single circular nozzle, for example an aeroramp injector, the throat diameter of the injector, $d_j$, is taken to be the diameter of a circle with the combined throat area of the individual jets making up the aeroramp. For example, if an aeroramp has 5 individual jets all with the same throat diameter, then $d_j$ would be the square root of 5 times the diameter of the throat diameter of the individual jets making up the aeroramp injector. In one embodiment aeroramp jets are used for the assembly of jets that are designed to have the furthest penetration.

$$\frac{y}{d_j} = a\left[\frac{(\rho v^2)_j}{(\rho v^2)_c}\right]^b M_j^c \theta^d \quad \text{Equation 1}$$

The injection of the feedstock along the perimeter of the feedstock injection zone 114 and at multiple transverse planes (represented by assemblies 122 and 124) result in increased mixing of the feedstock with the carrier stream, as compared to the prior art. Thorough mixing of the feedstock with the carrier stream is important to provide uniform composition and temperature distribution in the combined stream ahead of the reaction zone 118.

In some embodiments, the nozzles within one assembly may inject feedstock at different radial depths. In some embodiments, the number of nozzles in a given assembly may be 1 to 200. As would be appreciated by those skilled in the art, while the arrangement of nozzles are described as aligned in transverse planes (i.e., perpendicular to the longitudinal axis of the reactor 100), the nozzles may be distributed in any other manner within the feedstock injection zone 114 to achieve the angular distribution (i.e., different angular points at a given radial depth) and radial distribution (i.e., different radial depths at a given angular point) in the carrier stream. For example, instead of being arranged in transverse planes, the nozzles 128 may be arranged in a plane offset from the perpendicular by an angle, such as a plane angled 30 degrees off the transverse plane. Or, the nozzles 128 may be staggered at different locations on the feedstock injection zone 114.

The combined stream enters mixing zone 116 where the combined stream is further mixed as a result of turbulent flow in the stream. As a result of the arrangement and configuration of nozzles 128 and 130 to inject the feedstock at multiple locations within the carrier stream, the length of the mixing section necessary to fully mix the combined stream is reduced, as compared to traditional nozzle configurations. In one embodiment, the feedstock is fully injected between 1 and 10 pipe diameters (i.e., inner diameter of the injection zone) downstream of the first injection location. In other words, in FIG. 1, the distance between assembly 124 (the first injection point upstream) and assembly 122 (the last injection point downstream) is between 1 and 10 pipe diameters. In other embodiments, the feedstock is fully injected between 1 and 5 pipe diameters downstream of the first injection location. In yet other embodiments, the feedstock is fully injected less than 1 pipe diameter downstream of the first injection location.

The transverse cross section of the reactor 100 increases in the reactor zone 118 due to angled wall 127. As the mixed stream enters the reactor zone 118 and expands into the larger area, its velocity decreases.

In some embodiments, the velocity of the mixed stream remains at supersonic velocities within the reaction zone 118. The reduction in velocity of the carrier stream converts a portion of the kinetic energy in the stream into thermal energy. The product mixture is then reduced to subsonic flow and quenched in quench/recovery zone 120.

In some embodiments, the velocity of the mixed stream transitions from supersonic to subsonic within the reaction zone 118. At this transition point, a shockwave is formed, which results in a nearly instantaneous increase in the pressure and temperature of the mixed stream. In various embodiments, the temperature of the mixed stream immediately upstream of the shockwave is about 1500 K to 2000 K, as compared to about 1800 K to 2300 K immediately downstream of the shockwave. The conditions in the mixed stream downstream of the shockwave are favorable to the formation of acetylene.

In some embodiments, a shock train is formed at the point where the stream transitions from supersonic to subsonic flow. A shock train is a series of weak shockwaves that propagate downstream from the supersonic to subsonic transition point. Whereas a single shockwave will heat the mixture nearly instantaneously (at the location of the shockwave), a shock train will heat the mixture more gradually. Each shockwave in the shock train will increase the temperature of the stream.

The mixed stream is increased to a temperature sufficient to favor the formation of acetylene and to provide enough energy to satisfy the endothermic reaction.

In one embodiment, the product stream exits the reaction zone 118 and enters the quench/recovery zone 120 to rapidly cool the product stream. In one embodiment, the quenching zone 120 comprises at least one injection nozzle to spray the product stream with water. The product stream is recovered at the distal end of the reactor 100 as indicated by 132.

In an alternative embodiment the feedstock injection zone can be of an annular cross section. The fuel injection zone, combustion zone, expansion zone, mixing zone and reaction zone may alternatively be either annular or circular. The use of an annular feedstock injection zone reduces the crossflow distance that feed must be injected into the carrier stream. The inner annulus may also be equipped with similar feedstock injection nozzles and can be held in place with struts or secured at the inlet or outlet of the reactor. Struts can have internal channels to allow the flow of feed or coolant. In some embodiments the feedstock injection zone can have other non-circular cross sections that reduce the crossflow distance that feedstock must penetrate into the carrier stream, for example rectangular or elliptical. For the case of a feedstock injection zone with a non-circular cross section the pipe diameter will be understood to mean the hydraulic diameter of the feedstock injection zone.

Referring to FIG. 2(a), a three dimensional view of the injector assembly 124 of FIG. 1 is depicted. In one embodiment, the injector assembly 124 is a separate component disposed in the body of reactor 100. In one embodiment, the injector assembly 124 is integral with the body of reactor 100. In one embodiment, the injector assembly 124 comprises four nozzles 130, represented by circles. In different embodiments, the nozzles 130 are jets, angled jets, aeroramp jets, ramp jets, strut jets, cascade jets, diamond jets or a combination thereof.

Referring to FIG. 2(b), a three dimensional view of the injector assembly 122 of FIG. 1 is depicted. In one embodiment, the injector assembly 122 is a separate component disposed in the body of reactor 100. In one embodiment, the injector assembly 122 is integral with the body of reactor 100. In one embodiment, the injector assembly 122 comprises eight nozzles 128, represented by circles. In different embodiments, the nozzles 128 are jets, angled jets, aeroramp jets, ramp jets, strut jets, or a combination thereof.

Referring to FIG. 2(c), a transverse view of the injector assembly 124 of FIG. 1 and the performance of the injection nozzles is depicted. In one embodiment, the injection nozzles 130 (indicated by diamonds) are configured to inject ⅔ of the feedstock 202 into the carrier stream. In one embodiment to get uniform distribution of feedstock the injection nozzles are configured to inject to a radial depth that is proportional to the flow of feedstock. For the case of nozzles 130 the nozzles are designed to cover the inner ⅔ of the cross sectional area of the injection section. This corresponds to a diameter of $\sqrt{\tfrac{2}{3}}=0.81$ and the injected feedstock penetrates halfway into this area which corresponds to a diameter of about 0.40 of the injection section diameter to a radial depth of about 0.8 of the radius of the injection section. The target radial depth is indicated by broken line 206. The target penetration point for each individual nozzle is indicated by solid circles 204.

Referring to FIG. 2(d), a transverse view of the injector assembly 122 of FIG. 1 and the performance of the injection nozzles is depicted. In one embodiment, the injection nozzles 128 (indicated by squares) are configured to inject feedstock 222 into the carrier stream to a radial depth of about 0.1 of the radius of the injection section. The target radial depth is indicated by broken line 226. The target penetration point for each individual nozzle is indicated by empty circles 224.

Figure 3:
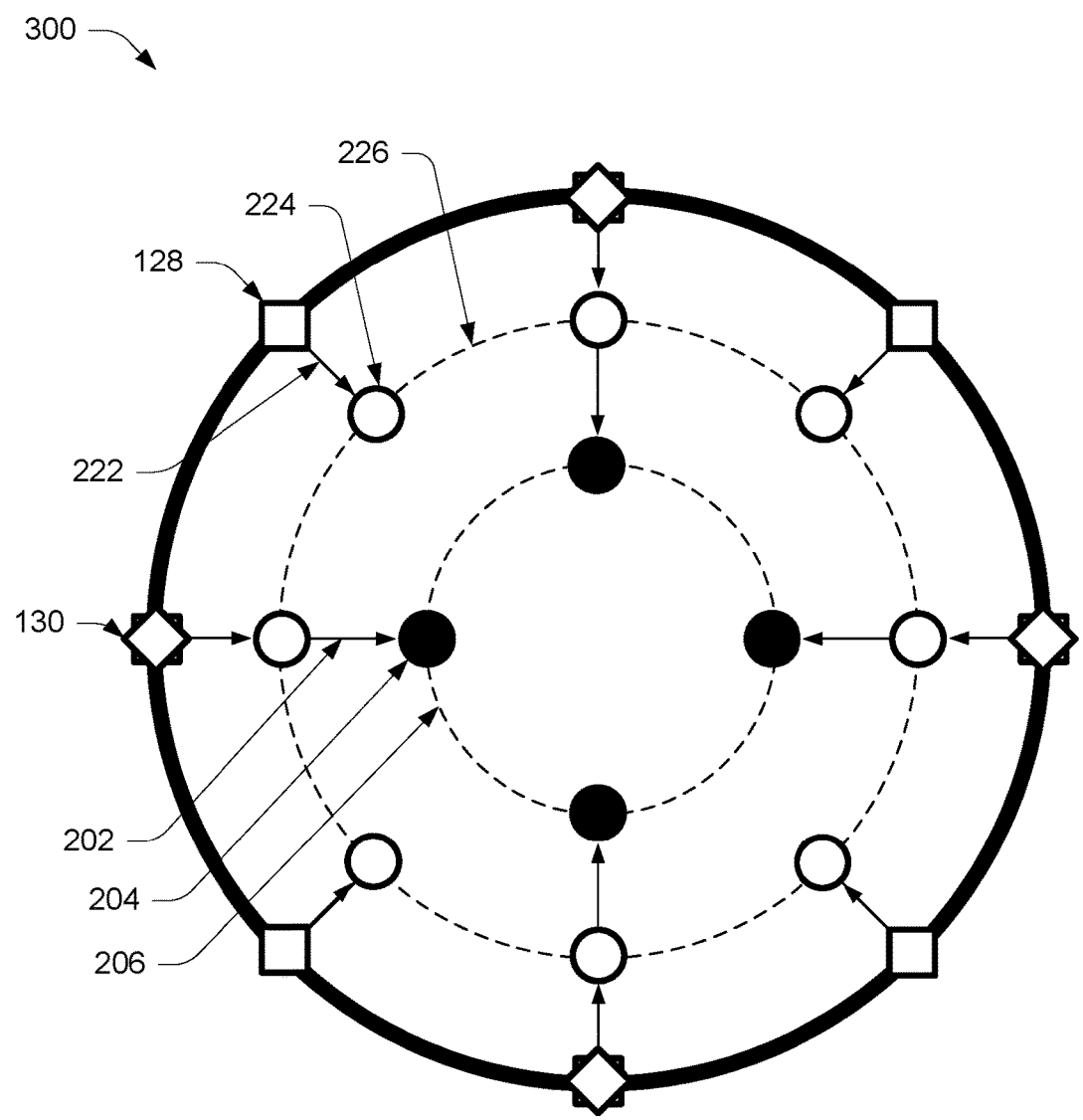
FIG. 3 shows the combined radial penetration of feedstock into the reactor body for the two assemblies of FIG. 1.

Referring to FIG. 3, the combined target distribution of feedstock into the reactor body using assemblies 122 and 124 is depicted. The nozzles 128 from assembly 122 inject feedstock 222 to numerous angular points 224 at a specific radial depth 226. The nozzles 130 from assembly 124 inject feedstock 202 to numerous angular points 204 at a specific radial depth 206.

The performance of each nozzle is configured to deliver the feedstock to the target location for a given carrier stream velocity. In certain embodiments, the penetration depth of each nozzle is monitored and dynamically adjusted to maintain the desired penetration depth. The target distribution pattern indicated by solid circles 204 (from assembly 124) and empty circles (from assembly 122) initially creates streams of high feedstock concentration within the carrier stream. These streams are quickly disbursed by the turbulent flow within the mixing section 116 and uniform mixing of the feedstock with the carrier stream is accomplished in very short order due to the even initial distribution of feedstock within the carrier stream.

In certain embodiments, a feedstock target radial penetration depth for each injection nozzle in the plurality of injection nozzles is different from a feedstock target radial penetration depth for all other injection nozzles in the plurality of injection nozzles. In certain embodiments, a jet diameter of injection nozzles in the first assembly is larger than a throat diameter of the nozzles in the second assembly. In certain embodiments, the injection pressure of the nozzles in the first assembly is greater than the injection pressure of the nozzles in the second assembly.

In certain embodiments, the first plane of feed injection nozzles is situated within an expanding nozzle. In certain embodiments, the second plane of feed injection nozzles is situated within an expanding nozzle. In certain embodiments, the third plane of feed injection nozzles is situated within an expanding nozzle.

Table 1 below provides one exemplary configuration of nozzles arranged in two transverse assemblies, where the velocity of the carrier stream is Mach 2.5, the first assembly comprises 4 nozzles and the second assembly comprises 8 nozzles.

TABLE 1

| Number of Jets in Assembly | Assembly Number (upstream to downstream) | Mach Number of Jet | Momentum of Fluid in Jets/ Momentum of Carrier Fluid | Injection Angle | Feedstock Flow/ Carrier Stream Flow | $d_j/D$ |
|---|---|---|---|---|---|---|
| 4 | 1 | 1 | 4 | 30 | 0.33 | 0.105 |
| 8 | 2 | 1 | 4 | 30 | 0.67 | 0.065 |

While the embodiments in FIGS. 1-3 describe a feedstock injector configuration comprising two assemblies, additional assemblies, each having additional nozzles, may be added to increase the distribution injection of feedstock into the carrier stream. For example, as the diameter of the reaction zone increases, additional injection assemblies, each injecting feedstock at a different radial depth, may be added to maintain the distribution of feed material and minimize the length of the mixing zone to achieve complete mixing.

Table 2 below provides one exemplary configuration of nozzles arranged in three transverse assemblies, where the velocity of the carrier stream is Mach 2.5, the first assembly comprises 2 aeroramp injectors with each aeroramp consisting of two nozzles separated by a distance of $5d_j$ with the upstream injector at an angle of 30° and the downstream nozzle of the aeroramp injector with an angle of 60°, the second assembly comprises 8 nozzles, and the third assembly comprises 16 nozzles.

TABLE 2

| Number of Jets in Assembly | Assembly Number (upstream to downstream) | Mach Number of Jet | Momentum of Fluid in Jets/ Momentum of Carrier Fluid | Injection Angle | Feedstock Flow/ Carrier Stream Flow | $d_j/D$ |
|---|---|---|---|---|---|---|
| 2 | 1 | 1 | 6 | 30, 60 | 0.2 | 0.082 |
| 8 | 2 | 1 | 4 | 30 | 0.4 | 0.071 |
| 16 | 3 | 0.33 | 3 | 30 | 0.4 | 0.033 |

Additional assembly configuration examples, with between 4 and 10 assemblies, are provided in Table 3 below. In various embodiments, the distance between the first upstream assembly and the last downstream assembly for the configurations below is between 0.5 to 5 pipe diameters. In various embodiments, the distance between the first upstream assembly and the last downstream assembly is between 0.1 to 4 pipe diameters.

TABLE 3

| Assembly Number | Number of Injector Nozzles | | | | | | |
|---|---|---|---|---|---|---|---|
| | 4 Assembly | 5 Assembly | 6 Assembly | 7 Assembly | 8 Assembly | 9 Assembly | 10 Assembly |
| 1 | 2 | 2 | 2 | 2 | 2 | 2 | 2 |
| 2 | 8 | 8 | 8 | 8 | 8 | 8 | 8 |
| 3 | 18 | 18 | 18 | 18 | 18 | 18 | 18 |
| 4 | 32 | 32 | 32 | 32 | 32 | 32 | 32 |
| 5 | — | 50 | 50 | 50 | 50 | 50 | 50 |
| 6 | — | — | 72 | 72 | 72 | 72 | 72 |
| 7 | — | — | — | 98 | 98 | 98 | 98 |
| 8 | — | — | — | — | 128 | 128 | 128 |
| 9 | — | — | — | — | — | 162 | 162 |
| 10 | — | — | — | — | — | — | 200 |

In one embodiment, the pyrolitic reactor described herein has a methane conversion greater than 50% and an acetylene selectivity greater than 50%.

What is claimed is:

1. A method to produce acetylene, comprising:
   introducing a fuel and an oxidizer into a fuel injection zone;
   combusting said fuel and said oxidizer in a combustion zone to create a carrier stream;
   accelerating the carrier stream to supersonic speed in an expansion zone;
   injecting first feedstock material using a first plurality of injection nozzles arranged annularly on a first transverse plane into a feedstock injection zone;
   delivering said first feedstock material from each of said first plurality of injection nozzles to a first radial depth within said carrier stream;
   injecting second feedstock material using a second plurality of injection nozzles annularly on a second transverse plane of the feedstock injection zone;
   delivering said second feedstock material from each of said second plurality of injection nozzles to a second radial depth within said carrier stream; and
   wherein a feedstock target radial penetration depth for each nozzle in said first and second plurality of injection nozzles is different from a feedstock target radial penetration depth for all other injection nozzles in said first and second plurality of injection nozzles.

2. The method of claim 1, further comprising transitioning, in a reaction zone, said carrier stream from supersonic speed to subsonic speed to create a shockwave.

3. The method of claim 1, further comprising transitioning, in a reaction zone, said carrier stream from supersonic speed to subsonic speed to create a shock train.

4. The method of claim 1, further comprising reducing a velocity of said carrier stream, in a reaction zone, to convert kinetic energy to thermal energy, while maintaining said velocity above supersonic speed.

5. The method of claim 1, wherein said first plurality of injection nozzles comprises at least two injection nozzles and said second plurality of injection nozzles comprises at least four injection nozzle.

6. The method of claim 1, wherein:
   said feedstock injection zone has a pipe diameter; and
   said first transverse plane is spaced from the second transverse plane by a distance of between about 0.5 to about 5 pipe diameters.

7. The method of claim 1, wherein said injecting feedstock further comprises:

providing third feedstock material to a third plurality of injection nozzles arranged annularly on a third transverse plane of the feedstock injection zone;

delivering said third feedstock material from each of said third plurality of injection nozzles to a third radial depth within said carrier stream; and said first transverse plane, said second transverse plane, and said third transverse plane are located within between about 0.5 to about 5 pipe diameters from each other.

8. The method of claim 1, further comprising introducing steam into said fuel injection zone.

9. The method of claim 1, wherein the feedstock injection zone comprises an annular cross section.

10. A method to produce acetylene, comprising:

introducing a fuel and an oxidizer into a fuel injection zone;

combusting said fuel and said oxidizer in a combustion zone to create a carrier stream;

accelerating the carrier stream to supersonic speed in an expansion zone;

injecting first feedstock material using a first plurality of injection nozzles arranged annularly on a first transverse plane into a feedstock injection zone;

delivering said first feedstock material from each of said first plurality of injection nozzles to a first radial depth within said carrier stream;

injecting second feedstock material using a second plurality of injection nozzles annularly on a second transverse plane of the feedstock injection zone;

delivering said second feedstock material from each of said second plurality of injection nozzles to a second radial depth within said carrier stream;

injecting third feedstock material using a third plurality of injection nozzles arranged annularly on a third transverse plane of the feedstock injection zone;

delivering said third feedstock material from each of said third plurality of injection nozzles to a third radial depth within said carrier stream; and said first transverse plane, said second transverse plane, and said third transverse plane are located within between about 0.5 to about 5 pipe diameters from each other.

11. The method of claim 10, further comprising transitioning, in a reaction zone, said carrier stream from supersonic speed to subsonic speed to create a shockwave.

12. The method of claim 10, further comprising transitioning, in a reaction zone, said carrier stream from supersonic speed to subsonic speed to create a shock train.

13. The method of claim 10, further comprising reducing a velocity of said carrier stream, in a reaction zone, to convert kinetic energy to thermal energy, while maintaining said velocity above supersonic speed.

14. The method of claim 10, wherein said first plurality of injection nozzles comprises at least two injection nozzles and said second plurality of injection nozzles comprises at least four injection nozzle.

15. The method of claim 10, further comprising introducing steam into said fuel injection zone.

16. The method of claim 10, wherein the feedstock injection zone comprises an annular cross section.

* * * * *